(12) United States Patent
Olsson et al.

(10) Patent No.: US 9,927,368 B1
(45) Date of Patent: Mar. 27, 2018

(54) SELF-LEVELING INSPECTION SYSTEMS AND METHODS

(75) Inventors: Mark S. Olsson, La Jolla, CA (US); Roger B. Shaffer, San Diego, CA (US); Stephanie M. Bench, Carlsbad, CA (US); Ray Merewether, La Jolla, CA (US); Michael Martin, San Diego, CA (US); David A. Cox, San Diego, CA (US)

(73) Assignee: SEESCAN, INC., San Diego, CA (US)

( * ) Notice: Subject to any disclaimer, the term of this patent is extended or adjusted under 35 U.S.C. 154(b) by 1059 days.

(21) Appl. No.: 13/358,463

(22) Filed: Jan. 25, 2012

Related U.S. Application Data

(60) Provisional application No. 61/436,593, filed on Jan. 26, 2011.

(51) Int. Cl.
| | |
|---|---|
| H04N 7/18 | (2006.01) |
| H04B 3/36 | (2006.01) |
| G01N 21/88 | (2006.01) |
| G01M 3/24 | (2006.01) |
| F16L 55/28 | (2006.01) |
| H04N 5/232 | (2006.01) |

(52) U.S. Cl.
CPC .......... G01N 21/8803 (2013.01); F16L 55/28 (2013.01); G01M 3/246 (2013.01); H04N 5/232 (2013.01)

(58) Field of Classification Search
CPC ............. G01N 21/8803; G01N 21/954; H04N 5/2252; H04N 5/232; F16L 55/28; F16L 2101/30; G01M 3/246; G01M 3/005; A61B 17/07207

USPC ........................................... 348/84–85; 455/7
See application file for complete search history.

(56) References Cited

U.S. PATENT DOCUMENTS

| | | | |
|---|---|---|---|
| 4,372,658 A | 2/1983 | O'Connor | |
| 6,611,661 B2 | 8/2003 | Buck | |
| 2005/0055356 A1* | 3/2005 | Tsai | 707/100 |
| 2005/0074140 A1* | 4/2005 | Grasso et al. | 382/103 |
| 2005/0275725 A1* | 12/2005 | Olsson et al. | 348/207.99 |
| 2010/0214306 A1* | 8/2010 | Kim | 345/560 |
| 2011/0006772 A1* | 1/2011 | Olsson et al. | 324/326 |
| 2012/0069172 A1* | 3/2012 | Hudritsch | 348/84 |
| 2013/0183023 A1* | 7/2013 | Sandrew et al. | 386/286 |

FOREIGN PATENT DOCUMENTS

GB 2342419 4/2000

OTHER PUBLICATIONS

Pearpoint, LTD., "Large Push-Rod Systems: P415 and P455," Catalog, 2009, pp. 15-16, www.Pearpoint.com.
Pearpoint, LTD., "P571," Specifications, 2007, 2 Pages, www.Pearpoint.com.

(Continued)

Primary Examiner — Tsion B Owens
(74) Attorney, Agent, or Firm — Steven C. Tietsworth, Esq.

(57) ABSTRACT

Self-leveling inspection systems for use in inspecting buried pipes or other cavities are disclosed. A camera head may include an image sensor, an orientation sensing module, and an image processing module configured to adjust an image or video provided from the image sensor, based at least in part on information provided from the orientation sensor, in the camera head.

38 Claims, 5 Drawing Sheets

(56) References Cited

OTHER PUBLICATIONS

Pearpoint, LTD., "P455: Rotational Twin View Colour Camera," Specifications, 2007, 3 Pages, www.Pearpoint.com.
Ridge Tool Company, "microExplorer Digital Inspection Camera," Operator's Manual, p. 12, Elyria, OH, USA.

* cited by examiner

SELF-LEVELING INSPECTION SYSTEMS AND METHODS

CROSS-REFERENCE TO RELATED APPLICATIONS

This application claims priority under 35 U.S.C. § 119(e) to U.S. Provisional Patent Application Ser. No. 61/436,593, filed Jan. 26, 2011, entitled SELF-LEVELING INSPECTION SYSTEMS & METHODS, the content of which is incorporated by reference herein in its entirety for all purposes.

FIELD

This disclosure relates generally to devices, systems, & methods for inspecting pipes or other cavities. More specifically, but not exclusively, the disclosure relates to a camera head configured to provide electronically level-adjusted images or video to a camera control unit or other system for display, storage, and/or transmission.

BACKGROUND

Pipe inspection systems for examining the interior of pipes, conduits, and other cavities or voids are known in the art. In order to correctly diagnose a defect within the interior of pipes, conduits, and other voids, a video camera linked to a push cable is generally employed. In a typical configuration, a rugged camera head connected to a push cable is sent through a pipe, and the camera head transmits video signals along a transmission medium to view the scene on a remote monitoring system. As the camera head snakes its way through the pipe, the camera head may rotate. Consequently, the scene transmitted to the remote monitoring system follows the motion of the camera head, and the image cannot maintain a frame of reference, such as an up-down orientation. Thus, it is desirable to orient the video such that the displayed images more closely approximate a level, upright viewing orientation.

There are various mechanical, electrical, and digital techniques available to rotate images recorded during pipe inspection in a camera control unit. However, prior art self-leveling pipe inspection camera systems have deficiencies. For example, the conventional approach for digitally rotating an image is to apply a transformation of coordinates from one coordinate system to a second, rotated, coordinate system. More specifically, the vector of coordinates for each pixel is multiplied by a rotation matrix. These computationally intense processes consume substantial memory resources, which may cause the video to have unacceptable latency when viewing in real-time.

Current techniques for reducing the consumption of memory resources include cropping, which presents the viewer with a cropped image, as well as rescaling, which presents viewers with an image scaled to fit within the constraints of the viewing area, thereby losing resolution. These lossy processes may achieve the goal of higher speed image data transmission, but at the expense of the image quality and/or the field of view.

SUMMARY

The present invention relates generally to a self-leveling pipe inspection system and associated camera head, transmission medium, camera control unit (CCU) and display. For example, in one aspect, the invention relates to a camera head for use in a pipe inspection system. The camera head may include an orientation sensing module, an image sensor configured to generate a source image comprising a first plurality of pixel values at a first pixel size of n horizontal pixels by m vertical pixels, and an image processing module coupled to the orientation sensing module and image sensor. The image processing module may include one or more processing elements and one or more memories. The image processing module may be configured to generate a second image corresponding to a subset of the first plurality of pixel values of the first image. The subset of pixels may be selected based at least in part on an orientation signal provided from the orientation sensing module.

In another aspect, the invention relates to a method of providing a display for pipe inspection. The method may include, for example, generating, at an image sensor, a first image including a first plurality of pixel values at a first pixel size of n horizontal pixels by m vertical pixels. The method may further include generating an orientation signal corresponding to an orientation of the image sensor, which may be a gravitation orientation. The method may further include generating a second image corresponding to a subset of the first plurality of pixel values of the first image. The subset of pixels may be generated based at least in part on the orientation signal. The second image may be provided as an image or frame of an output video signal. The output video signal may be an analog video signal, such as a composite video signal, a component video signal, an S-video signal, or other analog video signal. Alternately, or in addition, the output video signal may be a digital video signal.

In another aspect, the invention relates to a programmable logic device. The device may be configured to, for example, receive a first image comprising a first plurality of pixel values at a first pixel size of n horizontal pixels by m vertical pixels, receive an orientation signal corresponding to an orientation of the image sensor, such as a gravitational orientation, and generate a second image corresponding to a subset of the first plurality of pixel values of the first image. The second image may be based at least in part on the subset of the first plurality of pixel values may be generated based on the orientation signal. The second image may be generated at a pixel size of p horizontal pixels by q vertical pixels. In some implementations, both p and q may be less than both m and n, respectively or in combination.

In another aspect, the disclosure relates to a computer-readable medium. The medium may include instructions for causing a processor to receive a first image comprising a first plurality of pixel values at a first pixel size of n horizontal pixels by m vertical pixels, receive an orientation signal corresponding to an orientation of the image sensor, such as a gravitation orientation, and generate a second image corresponding to a subset of the first plurality of pixel values of the first image, wherein the subset of pixels are generated based at least in part on the orientation signal. The subset of pixels may be generated as a second pixel size of p horizontal pixels by q vertical pixels. In some implementations, both p and q may be less than n and m, respectively or in combination.

Various additional features, aspects, and embodiment and implementation details are further described below in conjunction with the appended Drawings.

BRIEF DESCRIPTION OF THE DRAWINGS

The present disclosure may be more fully appreciated in connection with the following detailed description taken in conjunction with the accompanying drawings, wherein.

DETAILED DESCRIPTION OF EMBODIMENTS

Figure 1:
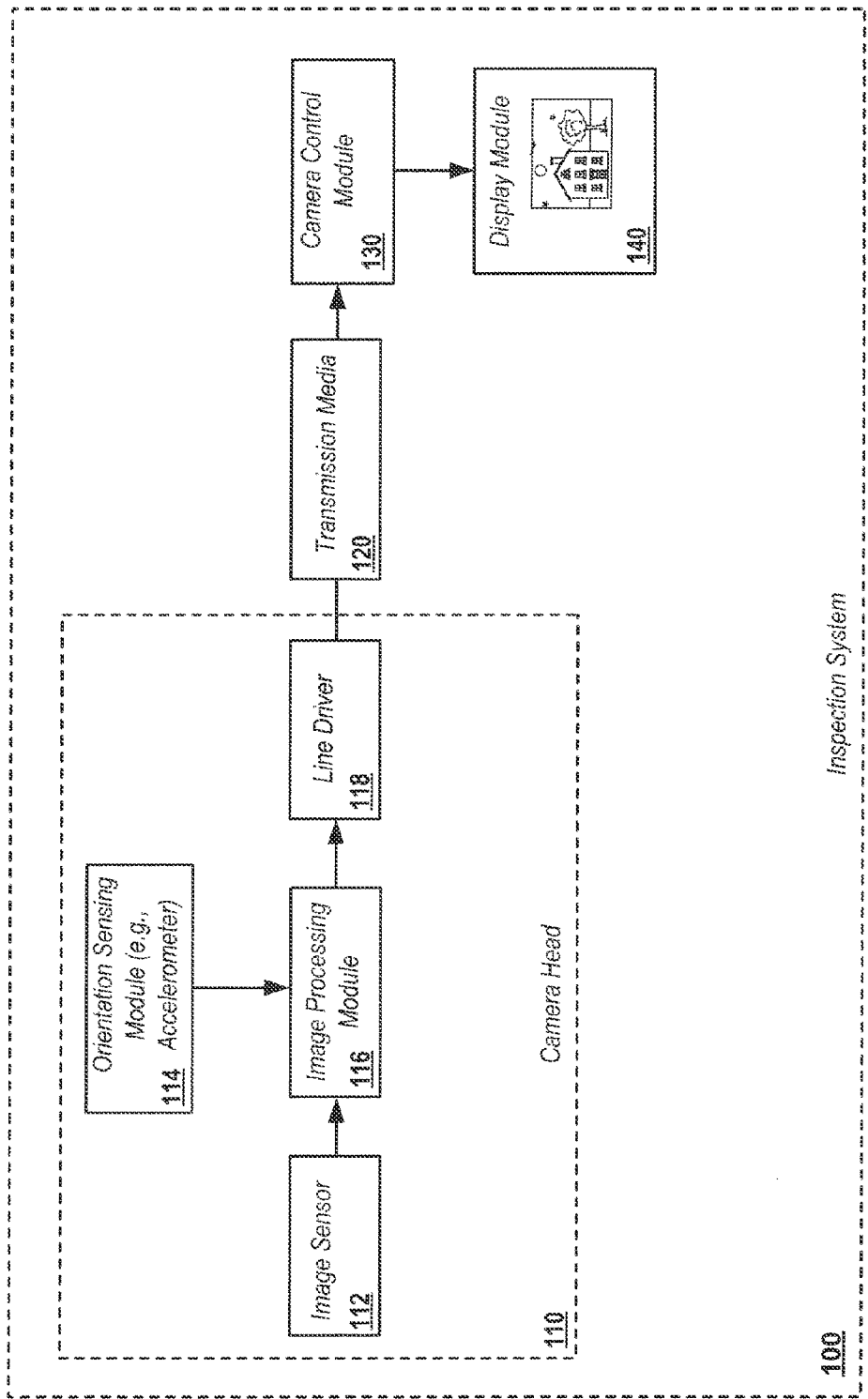
FIG. 1 is a block diagram illustrating details of an embodiment of a pipe inspection system.

The present disclosure relates generally to pipe inspection systems, apparatus, and methods that may be used for imaging of pipes, conduits, and/or other cavities or spaces using electronic self-leveling. Components of a self-leveling pipe inspection system may include camera heads, output signal transmission media, camera control units (CCUs), displays, and related components.

For example, in one aspect, the present disclosure relates to a camera head for use in a pipe inspection system. The camera head may include an orientation sensing module, an image sensor configured to generate a source image comprising a first plurality of pixel values at a first pixel size of n horizontal pixels by m vertical pixels, and an image processing module coupled to the orientation sensing module and image sensor. The image processing module may include one or more processing elements and one or more memories. The image processing module may be configured to generate a second image corresponding to a subset of the first plurality of pixel values of the first image. The subset of pixels may be selected based at least in part on an orientation signal provided from the orientation sensing module.

The camera head may further include a line driver coupled to the image processing module, wherein the image processing module is configured to provide the second image as an image and/or as a frame of an output video signal to the line driver.

The orientation sensing module may include, for example, an accelerometer or other motion or position sensing device(s). The accelerometer may be a 3-axis accelerometer. The pipe inspection system may further include a camera control unit coupled to the line driver module and a display integral with or coupled to the CCU. The display device may be configured to provide a visual display corresponding to the output video signal. For example, the display device may be configured to render the video signal and/or an image provided from the image processing module. The signal provided from the accelerometer may correspond to a gravitationally induced orientation of the accelerometer, which may correspond to an orientation of the image sensor, such as within a pipe, conduit, or other cavity.

In some implementations, the second image may, for example, be generated at a pixel size of p horizontal pixels by q vertical pixels, wherein both p and q are less than or equal to the smaller of m and n, respectively or in combination.

The image processing module may include, for example, a processing element and a memory element. The processing element may be configured to store the first plurality of pixel values of the first image in the memory element, determine ones of a plurality of virtual pixel values based on the first plurality of pixel values stored in the memory element, and generate the video signal based on the plurality of virtual pixel values. The processing element may include a programmable logic device such as a field programmable gate array (FPGA) or other logic device. Alternately, or in addition, the processing element may include an application specific integrated circuit (ASIC), a microprocessor, microcontroller, or digital signal processor (DSP).

The memory element may include, for example, a single memory set or memory array. The memory element may include a ping-pong memory set or memory array, where the memory array may be configured to allow writing of the first image into a first array of the ping-pong memory and reading the second image from a second array of the ping-pong memory. Buffers may be swapped in ping-pong memory configurations. In some implementations, a dual-port RAM or FIFO configuration may be used.

The ones of the plurality of virtual pixels may, for example, be determined as a predefined function of the first plurality of pixel values. The predefined function may be, for example, an average of one or a plurality of the first plurality of pixel values in proximity to the ones of the plurality of virtual pixels. The predefined function may be a bilinear interpolation, such as averaging only a ring of nearest neighbors of a missing color to fill in a missing color element. The predefined function may be a gradient-based or high quality linear interpolation or other function such as is known or developed in the graphics processing art. The images processing module may be further configured to perform demosaicing, rotation transformations, and/or resolution reduction.

The camera head may include, for example, a wide angle lens optically coupled to the image sensor. The wide angle lens may be configured to cover a diagonal field of view of about 90 degrees or more with a rear field of view that covers at least about 50 percent of an active imaging of the image sensor.

The image sensor may include, for example, a high resolution image sensor element having a resolution of 1600 by 1200 pixels or higher. The high resolution image sensor may include a charge coupled device (CCD), complementary metal oxide semiconductor (CMOS) sensor element or device, or other image sensing device.

In another aspect, the invention relates to a method of providing a display for pipe inspection. The method may include, for example, generating, at an image sensor, a first image including a first plurality of pixel values at a first pixel size of n horizontal pixels by m vertical pixels. The method may further include generating an orientation signal corresponding to an orientation of the image sensor, which may be a gravitation orientation. The method may further include generating a second image corresponding to a subset of the first plurality of pixel values of the first image. The subset of pixels may be generated based at least in part on the orientation signal. The second image may be provided as an image or frame of an output video signal. The output video signal may be an analog video signal, such as a composite video signal, a component video signal, an S-video signal, or other analog video signal. Alternately, or in addition, the output video signal may be a digital video signal.

The method may further include, for example, providing a display corresponding to the output video signal. The display may be provided by, for example, rendering the output video signal on a display device. The second image may be generated at a pixel size of p horizontal pixels by q vertical pixels. In some implementations, both p and q may be less than or equal to both m and n, respectively or in combination. The stage of generating a second image may include storing the first plurality of pixel values of the first image in the memory element, determining ones of a plurality of virtual pixel values based on the first plurality of pixel values stored in the memory element, and generating the second image based on a plurality of virtual pixel values. The ones of the plurality of virtual pixels may be determined as a predefined function of the first plurality of pixel values, such as an average of a plurality of one or more of the first plurality of pixel values in proximity to the ones of the plurality of virtual pixels. The predefined function may be a bilinear interpolation, such as averaging only a ring of nearest neighbors of a missing color to fill in a missing color element. The predefined function may be a gradient-based or high quality linear interpolation or other function such as is known or developed in the graphics processing art. The method may further include stages such as demosaicing, rotation transformations, and/or resolution reduction.

In another aspect, the invention relates to a programmable logic device. The device may be configured to, for example, receive a first image comprising a first plurality of pixel values at a first pixel size of n horizontal pixels by m vertical pixels, receive an orientation signal corresponding to an orientation of the image sensor, such as a gravitational orientation, and generate a second image corresponding to a subset of the first plurality of pixel values of the first image. The second image may be based at least in part on the subset of the first plurality of pixel values may be generated based on the orientation signal. The second image may be generated at a pixel size of p horizontal pixels by q vertical pixels. In some implementations, both p and q may be less than both m and n, respectively or in combination.

The generating a second image may include, for example, storing the first plurality of pixel values of the first image in the memory element, determining ones of a plurality of virtual pixel values based on the first plurality of pixel values stored in the memory element, and generating the second image based on a plurality of virtual pixel values. The ones of the plurality of virtual pixels may be determined as a predefined function of the first plurality of pixels. The predefined function may be an average of one or a plurality of the first plurality of pixel values in proximity to the ones of the plurality of virtual pixels. The predefined function may be a bilinear interpolation, such as averaging only a ring of nearest neighbors of a missing color to fill in a missing color element. The predefined function may be a gradient-based or high quality linear interpolation or other function such as is known or developed in the graphics processing art. The programmable logic device may be further configured to perform demosaicing, rotation transformations, and/or resolution reduction.

In another aspect, the disclosure relates to a computer-readable medium. The medium may include instructions for causing a processor to receive a first image comprising a first plurality of pixel values at a first pixel size of n horizontal pixels by m vertical pixels, receive an orientation signal corresponding to an orientation of the image sensor, such as a gravitation orientation, and generate a second image corresponding to a subset of the first plurality of pixel values of the first image, wherein the subset of pixels are generated based at least in part on the orientation signal.

The instructions may include, for example, instructions for generating the second image at a pixel size of p horizontal pixels by q vertical pixels. In some implementations, both p and q may be less than both m and n, respectively or in combination. The instructions may include instructions to generate the second image by storing the first plurality of pixel values of the first image in the memory element, determining ones of a plurality of virtual pixel values based on the first plurality of pixel values stored in the memory element, and generating the second image based on a plurality of virtual pixel values. The instructions may include instructions to determine ones of the plurality of virtual pixels as a predefined function of the plurality of pixel values, such as an average of one or a plurality of the first plurality of pixel values in proximity to the ones of the plurality of virtual pixels. The predefined function may be a bilinear interpolation, such as averaging only a ring of nearest neighbors of a missing color to fill in a missing color element. The predefined function may be a gradient-based or high quality linear interpolation or other function such as is known or developed in the graphics processing art. The instructions may further include instructions to perform demosaicing, rotation transformations, and/or resolution reduction.

Various additional aspects and details of self-leveling systems and methods that may be used in embodiments in conjunction with the disclosure herein are described in co-assigned U.S. patent application Ser. No. 10/858,628, filed Jun. 1, 2004, entitled SELF-LEVELING CAMERA, the entire disclosure of which is incorporated by reference herein in its entirety.

Various additional features, aspects, and embodiment and implementation details are further described below in conjunction with the appended Drawings.

In an exemplary embodiment, a pipe inspection system camera head may include elements or components for providing a digital image, such as an electronic image sensor using CCD, CMOS, or other image or video sensing and capture technologies, along with an orientation and/or position sensing module for providing orientation and/or position data associated with the position and/or orientation of the image sensor, which may be relative to a reference orientation such as that due to gravity (e.g., up/down relative to the earth's surface or a normal upright orientation).

Output images and/or video data from the image sensor may be provided, along with the orientation/position data and/or other data or information, such as audio information, other sensor data, and the like, to an image processing module, which may then provide an output video signal that is adjusted in the camera head for a desired orientation, such as an upright orientation relative to gravity.

The output video signal may then be provided to a camera control unit (CCU) or other system or device that includes display and/or storage capability. A visual display corresponding to the output video signal may then be provided, such as by rendering the output video signal on a display device of the CCU or other system such as an LCD display, and/or on other devices such as printer, and/or on another video or image output device. In addition, the image or video may also be stored for future display, output, transmission, processing, and/or analysis.

FIG. 1 illustrates one embodiment 100 of such an inspection system in accordance with various aspects. Inspection system 100 may include a camera head module 110 configured to mechanically house components such as an image sensor 112, an orientation and/or position sensing module 114, an image processing module 116, a line driver module 118, and/or other modules or components, such as power supplies, insulation elements, heating elements, defogging elements, lens elements, and the like (not shown). The camera head may be coupled to a push-cable or other mechanism for deploying or retracting the camera head from a pipe or other cavity.

The image sensor 112 may be, for example, a high resolution image sensor such as an OV9810 9-Megapixel 1080 HD Video Image Sensor, manufactured by the Omnivision® Company, and/or other image sensors known or developed in the art. In one embodiment, the image sensor may have an element array of n×m pixels, where n×m may be 3488×2616.

Orientation module 114 may include, for example, a sensing component such as an accelerometer, such as a three-axis accelerometer like the LSM303DLH, and/or other position and/or orientation elements known or developed in the art, such as compass sensors, inertial navigation sensors, and the like. Image processing module 116 may comprise, for example, a programmable logic device such as a Field Programmable Gate Array (FPGA), such as the Actel Igloo AGL250V2-CSG196I, one or more microcontrollers or microprocessors, digital signal processors (DSPs), ASICs, memory devices, and/or other electronic and processing components capable of being configured to receive, store, and process images such as described subsequently herein. Camera head 110 may further include one or more output circuits configured to provide image and/or video output, such as a line driver 118 as shown.

A transmission medium 120 may be used to connect the camera head 110 to a camera control module (CCU) 130 to carry the output signals. In an exemplary embodiment the transmission medium 120 may be a wired conductor configured to carry the output signal, however, in other embodiments the transmission medium may be a wireless medium, fiber optic medium, or other signal transmission medium. Camera control module 130 may include various components for controlling and monitoring camera operation and information, such as image or video resolution, lighting, zooming, and/or related operations or functions. A display module 140 may be coupled to and/or incorporated in control module 130 to render images and/or video provided from camera head 110. Control module 130 may include additional components such as memory for storing video and/or images and/or associated data or metadata, as well as components for providing other output such as digital video and/or image files, hard copy, or other data or information. The camera control module may further include one or more wired or wireless communication modules (not shown) for sending and/or receiving data from other devices or systems, such as cellular data communication modules, Wi-Fi or Wi-Max modules, ISM-band modules, Ethernet modules, USB or Firewire modules, or other communications modules.

Figure 3:
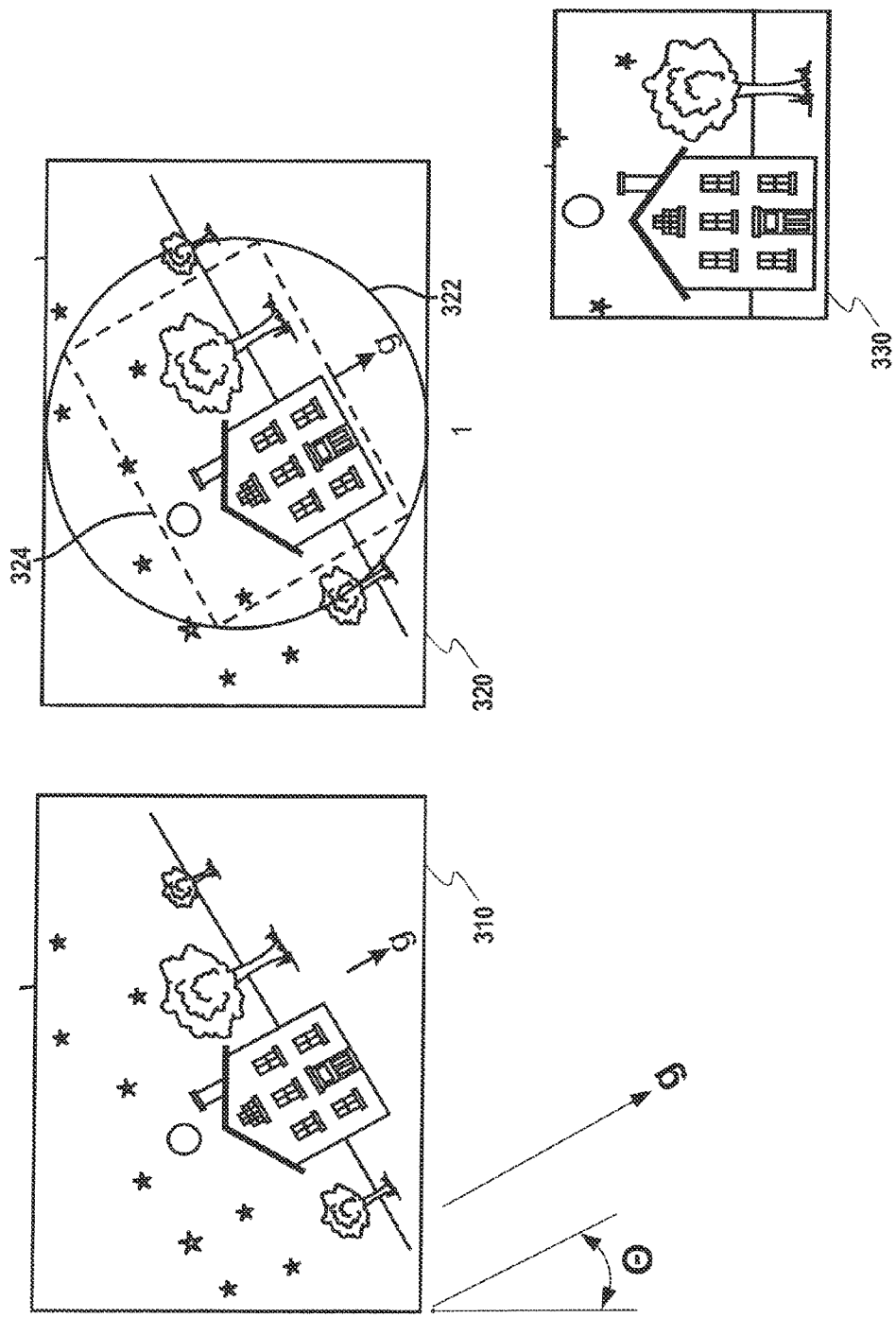
FIG. 3 illustrates details of an example image reorientation process consistent with aspects of the present invention.

In an exemplary embodiment, display module 140 is capable of rendering an orientation-adjusted output image or video corresponding to a raw image or video data provided from the image sensor 112, such as on an LCD or other display element. For example, a source image, such as example source image 310 as shown in FIG. 3, may be generated and provided from image sensor 112. The source image may be rotated, at an angular orientation theta (Θ) (as shown) relative to a reference orientation, which may correspond with a gravity-based vertical orientation (e.g., vertical or up-down with respect to the earth's gravitation force, g). The orientation may be sensed by orientation module 114, such as by a three-axis accelerometer or other orientation sensor, which may provide output data or information to image processing module 116 where it may be used to generate orientation adjusted output.

Figure 2:
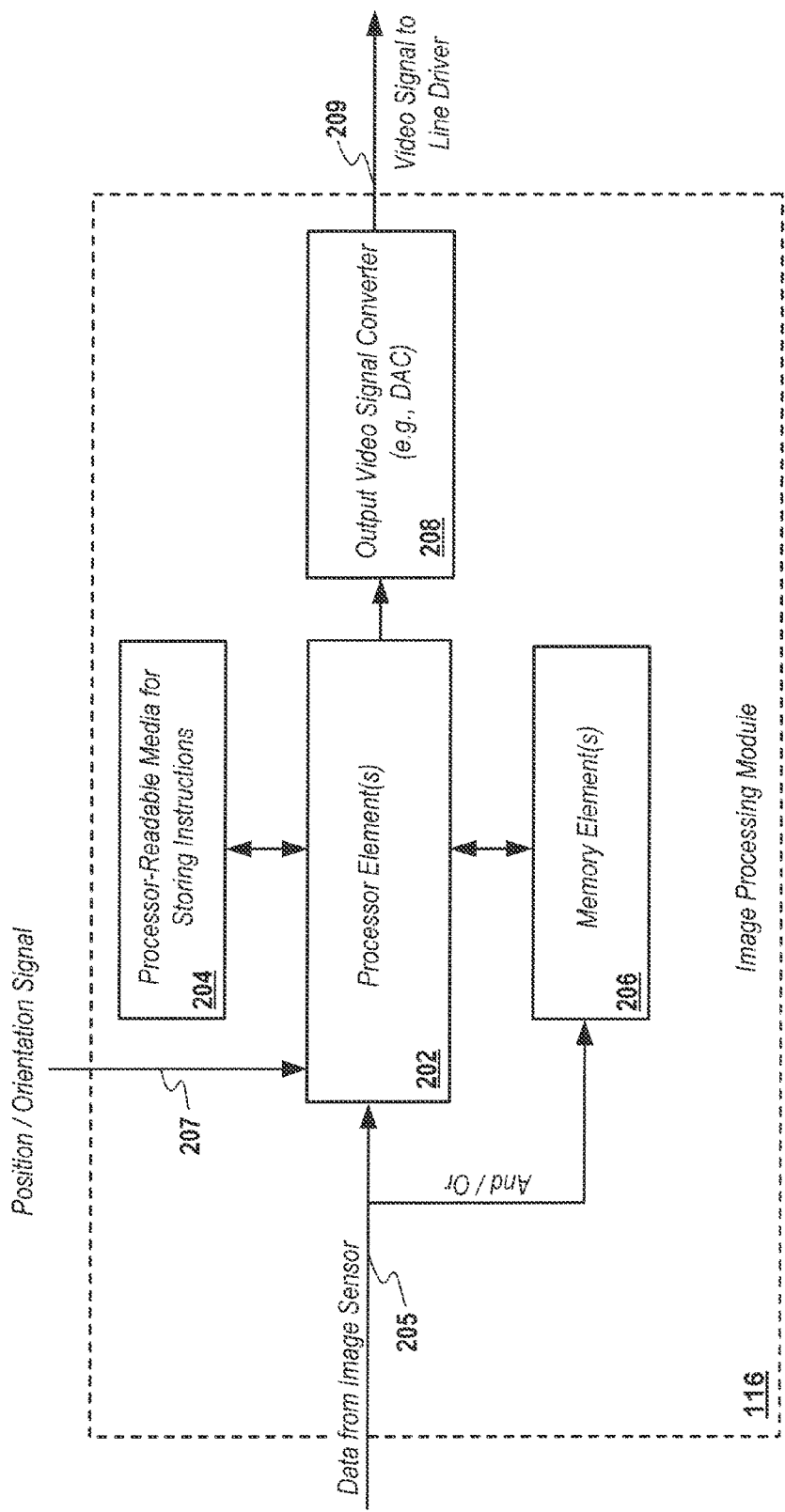
FIG. 2 illustrates details of an embodiment of a signal processing module for use in a camera head of a pipe inspection system such as shown in FIG. 1.

FIG. 2 illustrates details of an embodiment of an image processing module such as image processing module 116 of FIG. 1. Module 116 may include one or more processing elements 202, which may comprise microprocessors, microcontrollers, programmable logic devices, such as field programmable gate arrays (FPGAs), application specific integrated circuits (ASICs), and/or other programmable devices as are known or developed in the art. In the case of a microprocessor or similar or equivalent device, storage media 204 may be incorporated within and/or coupled externally to processor element 202 so as to store and provide instructions to the processor element 202 to perform the various signal processing functions as described subsequently herein. In some cases, the instructions may be incorporated within or integral to the processor element(s) 202, such as by being implemented in logic in a device such as an FPGA.

In operation, the image processing module 116 may receive a source image or sequence of images from image sensor 112, such as via data connection 205, and store the source image, such as example source image 310 of FIG. 3, to a memory element 206, which may be, for example, a single memory array or multiple memory arrays. The data may be transferred directly to the memory element 206, such as through direct memory access (DMA) via connection 205 and/or may be received by processor element 202 and then stored in memory element 206.

Processor element 202 may then generate an output image or sequence of images, such as in the form of a sequence of images or a video signal, where the output image or video signal is orientation-adjusted relative to the source images. Examples of embodiments of processing so as to generate the orientation adjusted output image(s) are described subsequently herein.

Image processing module 116 may further include an output video signal converter module 208, which may be configured to generate, either alone or in conjunction with the processor element 202, the orientation-adjusted output image(s) or video signal. For example, in one implementation, converter 208 includes a digital-to-analog converter (DAC) configured to receive pixels corresponding to the orientation-adjusted output image(s) or video signal and convert them to an analog or digital video signal in a standard or proprietary video format. For example, in an exemplary embodiment, a digital-to-analog converter may encode binary digital data into an analog video signal, such as a composite, component, S-Video, or other analog video signal, which may be, for example, in the National Television Systems (NTSC), Phase Alternate Line (PAL) format, and/or other image or video formats known or developed in the art. In some embodiments, digital images or digital video signals may alternately be provided as an output.

The output may then be coupled to a line driver, such as line driver 118 as shown in FIG. 1, which may then amplify and/or filter the video signal. This may be done to improve the quality of transmission of the output video signal over the transmission medium 120 to the camera control module 130 and/or display module 140. In an exemplary embodiment, transmission medium 120 is a conductor configured to carry video and/or data signals, however, in some embodiments it may be a fiber optic cable or other connection, such as a wireless connection.

After receipt of the output video signal at the CCU 130 (as shown in FIG. 1), an output display corresponding to the orientation adjusted image or video may be provided. For example, the output may be provided by rendering the orientation adjusted video output signal on display device 140, and/or the image or video may be stored on a computer storage media, provided as hard copy, output or transmitted to another device or system, or otherwise used for analysis of the pipe, conduit, or other void or cavity being inspected. Orientation adjustment performed in and provided from the camera head, rather than in the CCU or other devices, may advantageously improve overall pipe inspection system performance, increase system flexibility, reduce CCU and display complexity, size, and/or cost, and provide other advantages.

FIG. 3 illustrates details of image processing as may be implemented, for example, by system 100 and image processing module 116 of camera head 110. Image 310 is an example source image, such as may be provided from image sensor 112. The source image may be rotated at an angle Θ relative to an orientation reference, such as a gravitational force vector g (directed downward or normal to the earth's surface). For example, if the image sensor/camera head 110 were to be rotated at angle Θ while positioned above the earth's surface, a rotated image, such as image 310 may result. While the rotation may be apparent in image 310, if such a rotation occurs while the inspection system is in a pipe, conduit or other void, the rotation may not be apparent. In this case, orientation information as may be provided from orientation module 114 may be used to generate an orientation adjusted output image(s) or video signal in the camera head.

Image 320 illustrates additional details of features associated with image 310. In particular, in an exemplary embodiment, a circular area 322 may be defined within the boundaries of source image 310. The circular area may be characterized by a circular definitional parameter, such as a radius, circumference or diameter. Within circular area 322, a sub-image area 324 may be defined. Sub-image area 324 may be a square or rectangular area, in which case a diagonal (not shown) will correspond with a line drawn along the diameter of the circular area 322, thereby allowing sub-image area 324 to fit within circular area 322 at any rotation angle. Although the example circular area 322 is shown within the boundaries of the source image 310 area, in some embodiments the circular area may optionally be larger than the image area shown, such as to provide a slightly wider angle of view in certain dimensions or to otherwise provide additional image detail or features.

Consequently, a sub-image may be generated or extracted from the source image in a square or rectangular configuration at any rotational angle. If theta is known, such as from orientation module 114, an example orientation adjusted sub-image 330 may be generated or extracted from the example source image 310.

For example, in one embodiment, the rectangular rotated sub-image area 324 may have a diagonal resolution that is less than the horizontal and vertical resolution of the image sensor; thus, the rectangular rotated sub-image area 324 may rotate within the source image to any angle within circular area 322 to give a display image area 330. For example, if a device used to capture image has an element sensor array of n×m, where n×m is 1000×1000, and a display device used to view the display image only needs 640×480 pixels, then a sub-image area 324 with a diagonal of 800 pixels may be rotated within the source image 320 to any angle, and the display image 330 (corresponding to sub-image 324) may be transmitted without rescaling or cropping. Examples of methods for extracting the sub-image as an output from image processing module 116 are further described below with respect to FIG. 5.

Although the examples of FIG. 3 illustrate a sub-image area entirely within a circle within the image sensor, which may be used to provide the widest angle of imaging within the capabilities of the image sensor, in some embodiments other pixel areas within the image sensor may alternately be provided in an output image or video signal. For example, in some embodiments, a fraction of the image area, such as a half, third, quarter, etc., may be provided in the output video signal in an orientation adjusted fashion. These will generally be of a narrower angle that that shown in FIG. 3, although in some cases wider aspect ratios may be used for the output images or video signals.

Figure 4:
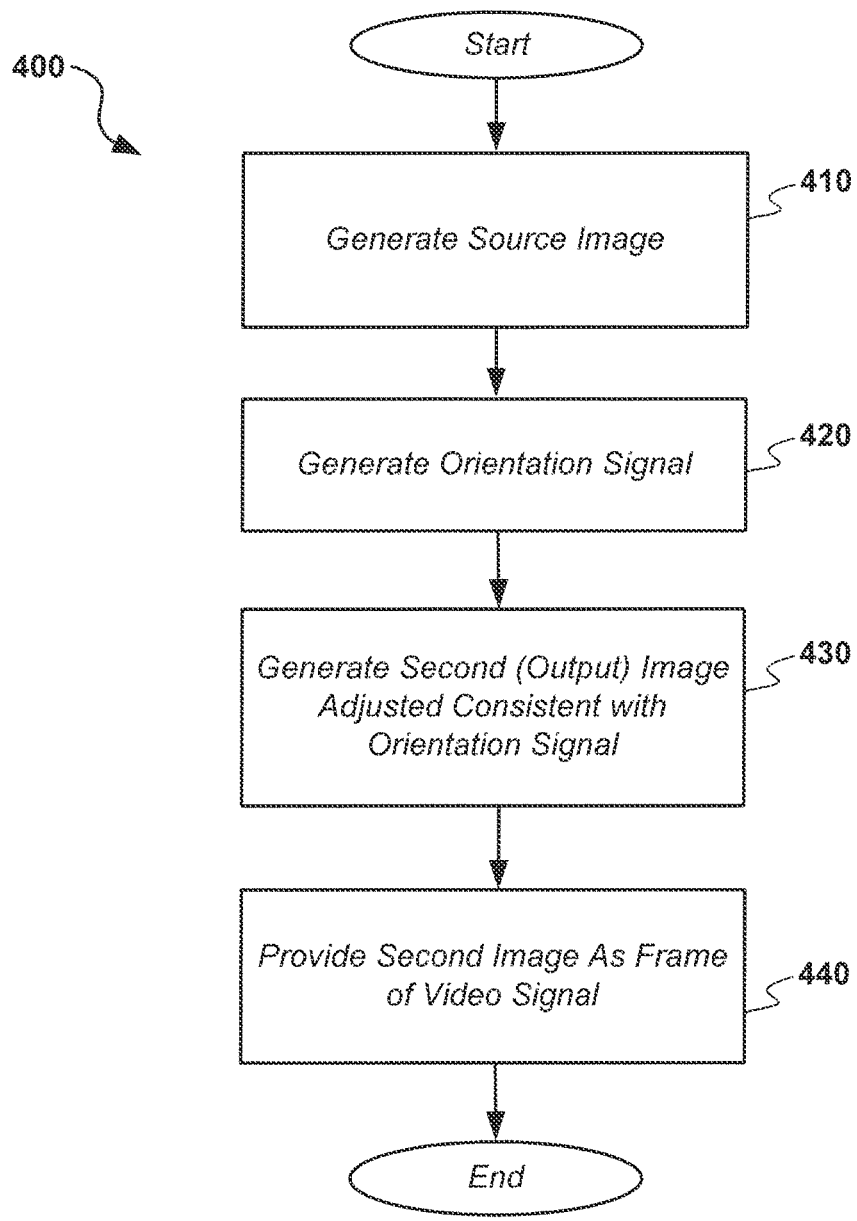
FIG. 4 illustrates details of an embodiment of a process for providing orientation adjusted images or video in a pipe inspection system such as shown in FIG. 1.

FIG. 4 illustrates details of an embodiment of a process 400 for generating an orientation adjusted output image, sequence of images or video signal, such as example sub-image 330 shown in FIG. 3. At stage 410, a source image or images may be generated, such as described previously with respect to FIG. 1. The source image(s) may be, for example, an image represented by a series of pixel values provided from a high definition image sensor, such as the OV9810 described previously. At stage 420, an orientation signal with orientation and/or positional data may be generated, such as from an accelerometer or other orientation or position sensing device. The orientation signal may be a gravitation orientation signal to provide an indication of offset of the imaging sensor from an up-down orientation.

The source image(s) and orientation signal may be provided to an image processing module, where a second or output image or images may be generated consistent with the orientation signal. Examples of various methods of generating the output signal are further described subsequently herein. At stage 440, the second or output image may be provided as an output signal, such as in the form of an image, series of images, or video signal. The video signal may be, for example, converted from a digital to an analog signal format, such as a composite video signal, component video signal, S-video signal, or other analog video signal. Data may be further embedded in the output video signal, such as in a blanking or synchronization interval in the analog video signal. The data may relate to orientation information, additional sensor information, audio data, position or motion data, position data associated with the second/output video frame sizing and/or orientation, or other data or information. In some implementations, the video output may be provided as an orientation-adjusted digital video signal.

Figure 5:
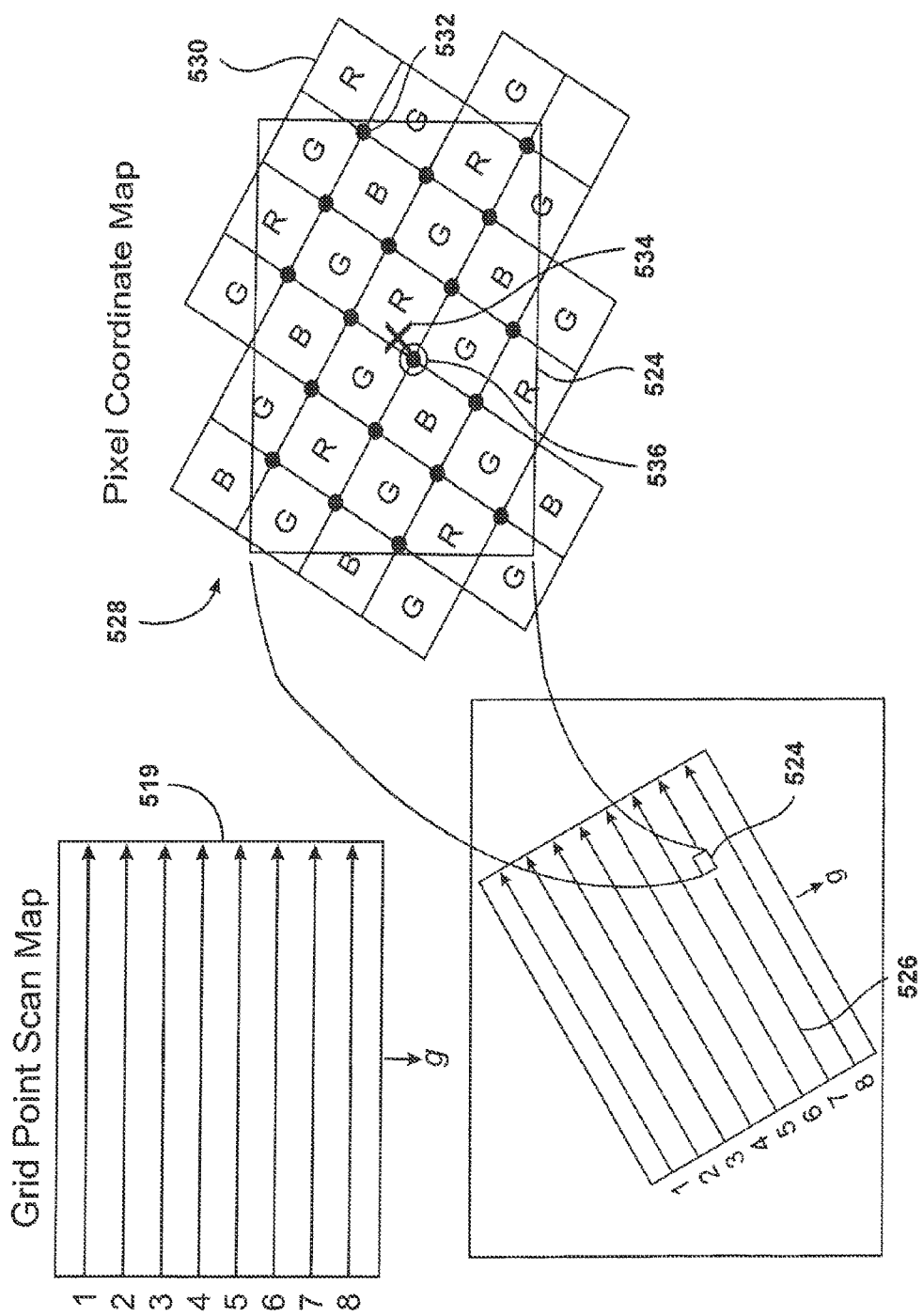
FIG. 5 illustrates details of one embodiment of signal processing to generate or extract an orientation adjusted image from a memory.

FIG. 5 illustrates details of an exemplary embodiment of image processing to generate a second or output image that is orientation adjusted relative to a first or source image. In one implementation, one or a plurality of pixel positions, such as pixel 524 (shown as representative of one of a plurality of pixels), may be determined to be used to scan a memory, such as a single memory set/memory array which may correspond with memory element 206 of FIG. 2

The basics of NTSC and PAL are similar in that a quadrature amplitude modulated (QAM) subcarrier carrying chrominance (I/Q) information is added to the luminance (Y) video signal to form a composite video baseband signal. For example, chrominance may be encoded using two 3.579545 MHz signals that are 90 degrees out of phase to each other, known as in-phase (I) and quadrature (Q). These two signals, I and Q, are amplitude modulated, and added together. The pixel positions for a composite output exist as points in time, and an instantaneous position of the continuously scanning beam. Luminance (Y) and chrominance (I/Q) may be encoded from a plurality of scan lines 526 to produce an output image (which may correspond with image 330 of FIG. 3).

In one implementation, a pixel coordinate map 528 may be used to illustrate the pixels from an image sensor, such as image sensor 112. The image sensor may include a Bayer filter to determine the color and intensity of virtual image pixel 524, which may be extracted from or determined by elements of the pixel coordinate map 528, such as by selecting values of one or more of the elements of coordinate map 528 and/or by generating the virtual image pixel as a function of one or more element values of the coordinate map. The Bayer filter is a pattern of individual filters, each of which are denoted with one letter selected from "R", "G", and "B" to indicate a red, a green, and a blue light transmission characteristic, respectively (see, for example, U.S. Pat. No. 3,971,065 of Bayer, the content of which is incorporated by reference herein in its entirety). The precise geometry of the virtual image pixels 524 can be mapped onto a grid 530 of fully and partially covered RGB array of the image sensor, where the virtual pixels may be represented by color and intensity values, with the color and intensity of the virtual image pixels 524 depending on its positioning on the grid 530. A coordinate 532 may be indicated at the vertex of a 2×2 RGB pixel block (and/or by a single pixel or other pixel block configurations) falling within or in proximity to one of the virtual image pixels 524. In one implementation, pixels may be selected for the virtual image based on a nearest neighbor or other vicinity mapping from the coordinate map to the virtual image pixel. Alternately, or in addition, pixel blocks may be averaged to calculate a color and an intensity associated with each of the virtual image pixels 524.

A centroid 534 may be determined and used to indicate a geometric center of the virtual image pixels 524. A neighboring coordinate 536 may be determined based on a relative location to the vertex of the pixel block nearest to the centroid 534. This neighboring coordinate 536 may be used to serve as the color and the intensity input for the virtual image pixels 524. In this case, processing some or all of the image pixels within the area of virtual pixel 524 may improve signal to noise ratio in the output image, which may subsequently improve the image and/or video quality at the display device or on a stored image or video signal.

In one exemplary embodiment, it may be desirable to have the diagonal of the rotated image be as close to the limiting dimension of the image sensor as is mathematically possible. This may be done to generate an output video signal with the widest field or angle of coverage. As shown in FIG. 3, the diagonal may be selected to correspond to the diameter of the circular area 322, however, in some cases, a larger diagonal may be selected so as to provide slight cropping at the corners of the rotated image. For example, a diagonal size may be selected to be slightly larger than the diameter of circle 322. In some embodiments, the centroid may be offset in one or both directions from the center of the image sensor, such as to image details or features offset from the center.

Alternately, or in addition, the diagonal size may be further selected based on the orientation signal provided from the accelerometer or other orientation sensor. In this case, if the image is only slightly rotated, the diagonal size may be selected to be larger as there will be less image cropping at the edges (compared to, for example, 90 degree rotation). As such, the size of the subset of pixels (e.g., number of pixels in the subset) may be based at least in part on the orientation signal, with more pixels used in the case of orientations close to the vertical. For example, if the image sensor is oriented at or close to vertical (e.g., the image from the image sensor is only slightly rotated from a level orientation) the size of the subset of pixels used may be larger than if the image sensor is rotated at a greater angle, which will then allow for a greater angle of coverage on the output video signal. Conversely, at the extreme, with a rectangular image sensor, the smallest pixel subset size would be selected when the sensor is rotated in the range of 90 degrees or 270 degrees, which would provide a narrower angle of coverage.

In some implementations, for maximum usable field of view, the diagonal of the rotated sub-image (in the pixel space of the high resolution image the virtual pixels of the transmitted image may be larger and fewer in number) may be approximately equal to the smallest of (m,n) of the high resolution image. In some implementations it may be desirable to slightly crop the corners of the rotated sub-image so as to maximize the field of view of the image inside the pipe, conduit, or other cavity.

In some implementations, output image size may be determined in accordance with a relationship such as $\lceil\sqrt{(p+q)}\rceil<(m,n)$. In another implementation, output image size may be determined in accordance with the relationship $\lceil\sqrt{(p+q)}\rceil<(m,n)/2$ or $\lceil\sqrt{(p+q)}\rceil<(m,n)/5$ (where "$\lceil$" and "$\rceil$" indicate an "upper ceiling"). Other output sizes may be used in various other embodiments.

Processing in RGB color space is generally inefficient and consumes substantial memory resources. Thus, to reduce consumption of memory resources, RGB color space may be converted directly to NTSC color space for transmission as a composite video output signal, such as is illustrated with respect to FIG. 1 and FIG. 2. For example, RGB color space may be converted directly to YCbCr color space for digital image processing; however, 4:1:1, 4:2:0, or 4:2:2 YCbCr data may be converted to 4:4:4 YCbCr data before undergoing conversion to NTSC or PAL signal format (YIQ or YUV). The transformations between each color space as disclosed herein, may be be carried out by methods known to one of skill in the art and routine modifications thereof, and/or according to procedures found in, for example, U.S. Pat. No. 7,015,962 of Acharya; U.S. Pat. No. 7,015,962 of Raffy et al.; and Jack, K. "Video Demystified", 2005, pp. 15-34 and 394-471, each of which is incorporated by reference herein.

In various embodiments, a color space transformation, such as YCbCr, YUV, or YIQ or chroma sub-sampling, such as 4:2:2, 4:2:0, or 4:1:1 may be used to produce an appropriate video output. These transformations and/or sub-sampling may be performed before or after the image (e.g., plurality of pixels) is stored in a memory such as memory element 206.

The term "level" or "leveled" may be used herein to describe a condition in which an object is substantially parallel relative to a horizontal plane and perpendicular to a gravitational force. For example, a flat surface on the earth normal to gravity may be a level surface.

The term "leveling" may be used in the sense of bringing an object to a position substantially parallel to a reference plane, that is, to make an object level.

The term "rotated" may be used herein to describe a condition in which an object is substantially parallel relative to a horizontal plane and perpendicular to gravity.

The term "camera head" may be used interchangeably with "camera," or "camera module." The terms "camera head" may be used herein to describe a device or module comprising an image sensor operably coupled to a lens, and may further include related or supporting electrical, optical, and/or mechanical components, such as a body or other structure and related components. The term "camera head" or "camera" may further be used herein to describe a composition comprising an image sensor operably coupled to a lens, an orientation sensor, a programmable device, such as a microprocessor, Field-Programmable Gate Array (FPGA), or DSP, as well a digital-to-analog converter and a line driver.

The term "high resolution image sensor" may be used herein to describe the resolution of the image sensor relative to the resolution of the remote monitoring system and/or display device. The term "high resolution image sensor" may be used herein to describe a semiconductor device that detects energy in the near infrared, infrared, visible, and/or ultraviolet spectrums to be used for the formation of a displayed image based on the detected energy. The detected energy may be used to form a single static image or a series of images (such as from a video camera) that may provide a moving image. Detection within the image sensor may be deployed in a planar arrangement in a two-dimensional orientation, where the detection devices (e.g. detection pixels) may be in rows and columns for digital video, or in horizontal lines slanted slightly downward for analog video. The term "high resolution image sensor" may refer to a complementary metal oxide semiconductor (CMOS), a charge-coupled detector (CCD), and/or other suitable high resolution image sensors or other detection devices.

The high resolution image sensor may be, for example, a complementary metal oxide semiconductor (CMOS). The complementary metal oxide semiconductor (CMOS) may have an element array of n rows of pixels by m columns of pixels (n×m) where n×m is at least 1600×1200.

The complementary metal oxide semiconductor (CMOS) may further have an element array configuration such as, but not in any way limited to: 1600×1200, 2048×1536, 2240×1680, 2560×1920, 3032×2008, 3072×2304, 3264×2448, 3488×2616, 4368×2912, 5616×3744, and/or 13280×9184 pixels. In one exemplary embodiment the complementary metal oxide semiconductor (CMOS) has an element array of 3488×2616. The complementary metal oxide semiconductor (CMOS) may be, for example, an OV9810 9-Megapixel 1080 HD Video Image Sensor, manufactured by the Omnivision® Company.

The term "accelerometer" is used to refer to a device that is capable of providing data related to a physical orientation and/or a position of an image sensor with respect to gravitational forces ("gravity"). Other suitable examples of orientation sensing devices that may be used are, for example, an inclinometer, a gyroscope, a magnetometer, a tilt sensor, and/or other orientation and/or position sensing devices known or developed in the art. An "accelerometer" may refer, for example, to a three-axis accelerometer, a two-axis accelerometer, and/or a one-axis accelerometer. The term "three-axis accelerometer" may be a single orientation sensor capable of measuring three perpendicular axes or acceleration and is interchangeable with three separate accelerometers arranged on three perpendicular axes.

The term "angular orientation" refers to the angle to which the image sensor is oriented with respect to gravity, g, the image recorded by the image sensor with respect to gravity, g, and/or the image to be displayed on a remote monitoring system with respect to gravity, g. Display orientation is generally independent of the physical orientation of the image sensor as might be sensed by an orientation sensor.

The term "field programmable gate array" or ("FPGA") may be used herein to describe a semiconductor device containing an array of programmable logic components, such as logic blocks, and programmable interconnects there between. Logic blocks can be programmed to perform the function of basic logic gates and/or relatively more complex combinational functions. The FPGA logic blocks may also include volatile and/or non-volatile memory elements. A hierarchy of programmable interconnects allows logic blocks to be interconnected and programmed after the FPGA is manufactured to implement any logical function.

The term "single memory array" may refer to an array of memory locations of one or more memory devices sufficiently large to hold a single n×m image or frame of video.

The term "composite video signal" may refer to a format or formats of analog video in which luminance data (brightness), chrominance data (color), and synchronization data (horizontal sync, vertical sync, and color reference bursts) are embedded in a single line-level signal. Analog video is discrete in the vertical dimension (there are distinct lines), but continuous in the horizontal dimension (every point blends into the next with no boundaries), hence there are no pixels in this format. The term "composite video signal" may refer to an analog encoding system or formatting standards for broadcast television systems. The term "composite video signal" may refer to a standard analog video format, such as Electronic Industry Association (EIA), National Television System Committee (NTSC), Comittee Consultatif International Radiotelecommunique (CCIR), Phase Alternate Line (PAL), and/or Sequential Color with Memory (SECAM).

The composite video signal may be, for example, an NTSC signal, which is used in most of North America and South America. The NTSC standard most commonly employed is an interlaced system where each frame is scanned for two fields at 262.5 lines per field, and is combined to display a frame of video with 525 horizontal scan lines slanting slightly downward from left to right. NTSC scans at 29.97 frames per second, with 59.94 fields displayed per second.

The term "field" refers to a set of even lines and/or odd lines. One field contains all the odd lines of the image; and the other field contains all the even lines of the image. The odd and even lines are displayed sequentially, thus interlacing a full frame. One full frame is produced by two interlaced fields, and is displayed approximately every $\frac{1}{30}$ of a second. Fields can be interlaced or progressively scanned depending on the video standard used.

In various embodiments, digital self-leveling pipe inspection camera systems consistent with the present invention are subject to a wide variety of modifications not described above. For example, the digital self-leveling pipe inspection camera system may be utilized in applications not associated with pipe inspection, such as assembly line monitoring, endoscopy, and/or other inspection or analysis applications.

The word "exemplary" is used herein to mean "serving as an example, instance, or illustration." Any aspect and/or embodiment described herein as "exemplary" is not necessarily to be construed as preferred or advantageous over other aspects and/or embodiments.

In some configurations, the various systems and modules include means for performing various functions as described herein. In one aspect, the aforementioned means may be a processor or processors and associated memory in which embodiments reside, and which are configured to perform the functions recited by the aforementioned means. The aforementioned means may be, for example, processors, logic devices, memory, and/or other elements residing in a camera head, camera control module, display module, and/or other modules or components as are described herein. In another aspect, the aforementioned means may be a module or apparatus configured to perform the functions recited by the aforementioned means.

In one or more exemplary embodiments, the functions, methods and processes described may be implemented in hardware, software, firmware, or any combination thereof. If implemented in software, the functions may be stored on or encoded as one or more instructions or code on a computer-readable medium. Computer-readable media includes computer storage media. Storage media may be any available media that can be accessed by a computer. By way of example, and not limitation, such computer-readable media can include RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

It is understood that the specific order or hierarchy of steps or stages in the processes and methods disclosed are examples of exemplary approaches. Based upon design preferences, it is understood that the specific order or hierarchy of steps in the processes may be rearranged while remaining within the scope of the present disclosure. The accompanying method claims present elements of the various steps in a sample order, and are not meant to be limited to the specific order or hierarchy presented unless explicitly noted.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the disclosure.

The various illustrative logical blocks, modules, and circuits described in connection with the embodiments disclosed herein may be implemented or performed in a processing element with a general purpose processor, digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

As used herein, computer program products comprising computer-readable media including all forms of computer-readable medium except, to the extent that such media is deemed to be non-statutory, transitory propagating signals.

The previous description of the disclosed aspects is provided to enable any person skilled in the art to make or use embodiment of the present invention. Various modifications to these aspects will be readily apparent to those skilled in the art, and the generic principles defined herein may be applied to other aspects without departing from the spirit or scope of the invention. Accordingly, the scope of the invention is not intended to be limited to the aspects shown herein, but is to be accorded the widest scope consistent with the specification and drawings, wherein reference to an element in the singular is not intended to mean "one and only one" unless specifically so stated, but rather "one or more." Unless specifically stated otherwise, the term "some" refers to one or more. A phrase referring to "at least one of" a list of items refers to any combination of those items, including single members. As an example, "at least one of: a, b, or c" is intended to cover: a; b; c; a and b; a and c; b and c; and a, b and c.

The previous description of the disclosed aspects is provided to enable any person skilled in the art to make or use the present disclosure. Various modifications to these aspects will be readily apparent to those skilled in the art, and the generic principles defined herein may be applied to other aspects without departing from the spirit or scope of the disclosure. Thus, the present invention is not intended to be limited to the aspects and details shown herein but is to be accorded the widest scope consistent with the appended claims and their equivalents.

We claim:

1. A pipe inspection system, comprising:
   a camera head, the camera head including:
   an orientation sensing module;
   an image sensor configured to generate a source image comprising a first plurality of pixel values at a first pixel size of n horizontal pixels by m vertical pixels and provide the source image as a source image output signal;
   an image processing module coupled to the orientation sensing module and image sensor, said image processing module configured to receive the source image output signal and generate a second image corresponding to a subset of the first plurality of pixel values of the first image, wherein the subset of pixels are selected based on a geometric rotation of the orientation of the source image output signal that is based on an orientation signal provided from the orientation sensing module, and provide the subset of pixels as a rotated digital output signal; and
   a line driver coupled to an output of the image processing module to receive the rotated digital output signal and provide a digital camera head output signal to a push-cable transmission line operatively coupled to the camera head.

2. The system of claim 1, wherein the output video signal is a digital video signal.

3. The system of claim 1, wherein the orientation sensing module comprises an accelerometer.

4. The system of claim 3, wherein the accelerometer is a 3-axis accelerometer.

5. The system of claim 1, further comprising: the push-cable: a camera control module coupled to an output of the push-cable and a display device coupled to the camera control module, the display device configured to render a visual display corresponding to the digital output video signal.

6. The system of claim 3, wherein the orientation signal is an accelerometer signal associated with a gravitationally induced orientation of the accelerometer corresponding to an orientation of the image sensor.

7. The system of claim 1, wherein the second image is generated at a pixel size of p horizontal pixels by q vertical pixels, wherein p and q are respectively less than m and n.

8. The system of claim 1, wherein the image processing module comprises a processing element and a memory element coupled to the processing element, said processing element configured to:
   store the first plurality of pixel values of the first image in the memory element;
   determine ones of a plurality of virtual pixel values based on the first plurality of pixel values stored in the memory element; and
   generate the video signal based on the plurality of virtual pixel values.

9. The system of claim 8, wherein the processing element comprises a programmable logic device.

10. The system of claim 8, wherein the programmable logic device comprises a field programmable gate array (FPGA).

11. The system of claim 8, wherein the processing element comprises an application specific integrated circuit (ASIC).

12. The system of claim 8, wherein the processing element comprises a microprocessor, microcontroller, or digital signal processor (DSP).

13. The system of claim 8, wherein the memory element comprises a single memory set or memory array.

14. The system of claim 8, wherein the memory element comprises a ping-pong memory set or memory array, wherein the memory array is configured to allow writing of the first image into a first array of the ping-pong memory and reading the second image from a second array of the ping-pong memory.

15. The system of claim 8, wherein ones of the plurality of virtual pixels are determined as a predefined function of the first plurality of pixel values in proximity to the ones of the plurality of virtual pixels.

16. The system of claim 15, wherein the predefined function is an average of a plurality of the first plurality of pixel values in proximity to the ones of the plurality of virtual pixels.

17. The system of claim 15, wherein the predefined function is a gradient based function.

18. The system of claim 15, wherein the predefined function is a bilinear interpolation.

19. The system of claim 1, wherein the camera head further includes a wide angle lens optically coupled to the image sensor.

20. The system of claim 19, wherein the wide angle lens is configured to cover a diagonal field of view of about 90 degrees or more with a rear field of view that covers at least about 50 percent of an active imaging of the image sensor.

21. The system of claim 1, wherein the image sensor comprises a high resolution image sensor of having a resolution of 1600 by 1200 pixels or higher.

22. The system of claim 21, wherein the high resolution image sensor comprises a charge coupled device (CCD).

23. The system of claim 21, wherein the high resolution image sensor comprises a complementary metal oxide semiconductor (CMOS) sensor.

24. The system of claim 1, wherein the size of the subset of pixels is based at least in part on the orientation signal.

25. The system of claim 24, wherein the size of the subset of pixels is a function of the offset in orientation of the image sensor from a gravity-referenced vertical orientation.

26. The system of claim 1, wherein the image processing module includes one or more non-transitory processor readable media having instructions for implementing at least in part the stages of:
   generating, at an image sensor in a camera head, a first image comprising a first plurality of pixel values at a first pixel size of n horizontal pixels by m vertical pixels;
   generating an orientation signal corresponding to an orientation of the image sensor;
   generating, in the camera head, a second image corresponding to a subset of the first plurality of pixel values of the first image, wherein the subset of pixels are generated based at least in part on the orientation signal; and
   providing the second image as a frame of an output video signal.

27. The system of claim 26, wherein the orientation is a gravitational orientation.

28. The system of claim 26, wherein the output video signal is generated as an analog video signal.

29. The system of claim 26, wherein the output video signal is generated as a digital video signal.

30. The system of claim 26, further comprising instructions for generating, on a display device, a visual display corresponding to the output video signal.

31. The system of claim 26, wherein the second image is generated at a pixel size of p horizontal pixels by q vertical pixels, wherein p and q are respectively less m and n.

32. The system of claim 26, wherein the instructions further include instructions for:
   storing the first plurality of pixel values of the first image in the memory element;
   determining, in a processing element, ones of a plurality of virtual pixel values based on the first plurality of pixel values stored in the memory element; and
   generating the second image based on a plurality of virtual pixel values.

33. The system of claim 32, wherein ones of the plurality of virtual pixels are determined as a predefined function of the first plurality of pixel values in proximity to the ones of the plurality of virtual pixels.

34. The system of claim 33, wherein the predefined function is an average of a plurality of the first plurality of pixel values in proximity to the ones of the plurality of virtual pixels.

35. The system of claim 1, wherein the image processing module is further configured to:
   receive a first image comprising a first plurality of pixel values at a first pixel size of n horizontal pixels by m vertical pixels;
   receive an orientation signal corresponding to an orientation of the image sensor;
   generate a second image corresponding to a subset of the first plurality of pixel values of the first image, wherein the subset of pixels are generated based at least in part on the orientation signal; and
   provide the second image as an output signal to a camera control unit.

36. The system of claim 35, wherein the second image is provided as a frame of a video output signal.

37. The system of claim 35, wherein the second image is provided as an output signal in a predefined image format.

38. The system of claim 1, wherein the image processing element includes a non-transitory processor readable media including instructions for causing a processor to:
- receive a first image comprising a first plurality of pixel values at a first pixel size of n horizontal pixels by m vertical pixels;
- receive an orientation signal corresponding to an orientation of the image sensor; and
- generate a second image corresponding to a subset of the first plurality of pixel values of the first image, wherein the subset of pixels are generated based at least in part on the orientation signal.

* * * * *